US00PP32111P2

(12) United States Plant Patent
Conner

(10) Patent No.: US PP32,111 P2
(45) Date of Patent: Aug. 25, 2020

(54) MUSCADINE GRAPE PLANT NAMED 'GA. 8-1-338'

(50) Latin Name: ***Vitis rotundifolia* Michx.**
Varietal Denomination: Ga. 8-1-338

(71) Applicant: University of Georgia Research Foundation, Inc., Athens, GA (US)

(72) Inventor: Patrick J. Conner, Tifton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 16/602,649

(22) Filed: Nov. 14, 2019

(51) Int. Cl.
*A01H 6/88* (2018.01)
*A01H 5/08* (2018.01)

(52) U.S. Cl.
USPC ..... Plt./206

(58) Field of Classification Search
USPC ..... Plt./206
CPC ..... A01H 6/88; A01H 5/08
See application file for complete search history.

(56) References Cited

PUBLICATIONS

American Society for Horticultural Science. Rubycrisp a New Home Garden Muscadine grape with Hermaphroditic Flowers and Large Red Berries Patrick J. Conner . Jul. 23, 2019.*

* cited by examiner

*Primary Examiner* — Annette H Para
(74) *Attorney, Agent, or Firm* — Klarquist Sparkman, LLP

(57) ABSTRACT

A new and distinct muscadine grape plant, substantially as herein illustrated and described, characterized by dark red-colored berries; self-fertile flowers; berries that separate with a high percentage of dry stem scars; berries that are very large in size, and very productive vines with high total and usable yields.

4 Drawing Sheets

BRIEF SUMMARY

The present invention comprises a new and distinct plant cultivar of *Vitis rotundifolia* Michx., which has been given the name 'Ga. 8-1-338'. My new variety has been asexually propagated in Tifton, Ga. by rooting cuttings under mist in the summer. The following unique combination of traits have been observed in the original plant of my variety and in asexually propagated progeny, are firmly fixed, and which in combination distinguish it from existing cultivars:

1) Self-fertile flowers in combination with very large (approx. 15 grams) berry weight.
2) Dark red-colored berries.
3) Berries with a firm flesh and crisp skin.
4) Berries with a high soluble solids content (brix).

BRIEF DESCRIPTION OF THE DRAWINGS

In FIG. 3, millijoules of force is presented on the y-axis and flesh maximum force in Newtons on the x-axis as determined by a texture analyzer.

FIGS. 1, 2 and 4 show the colors of the new variety as close to true color as is reasonably possible to obtain in colored reproductions of this type. Actual leaf and fruit colors may differ from leaf and fruit colors in the photographs due to light and environmental factors.

BACKGROUND

Figure 1:
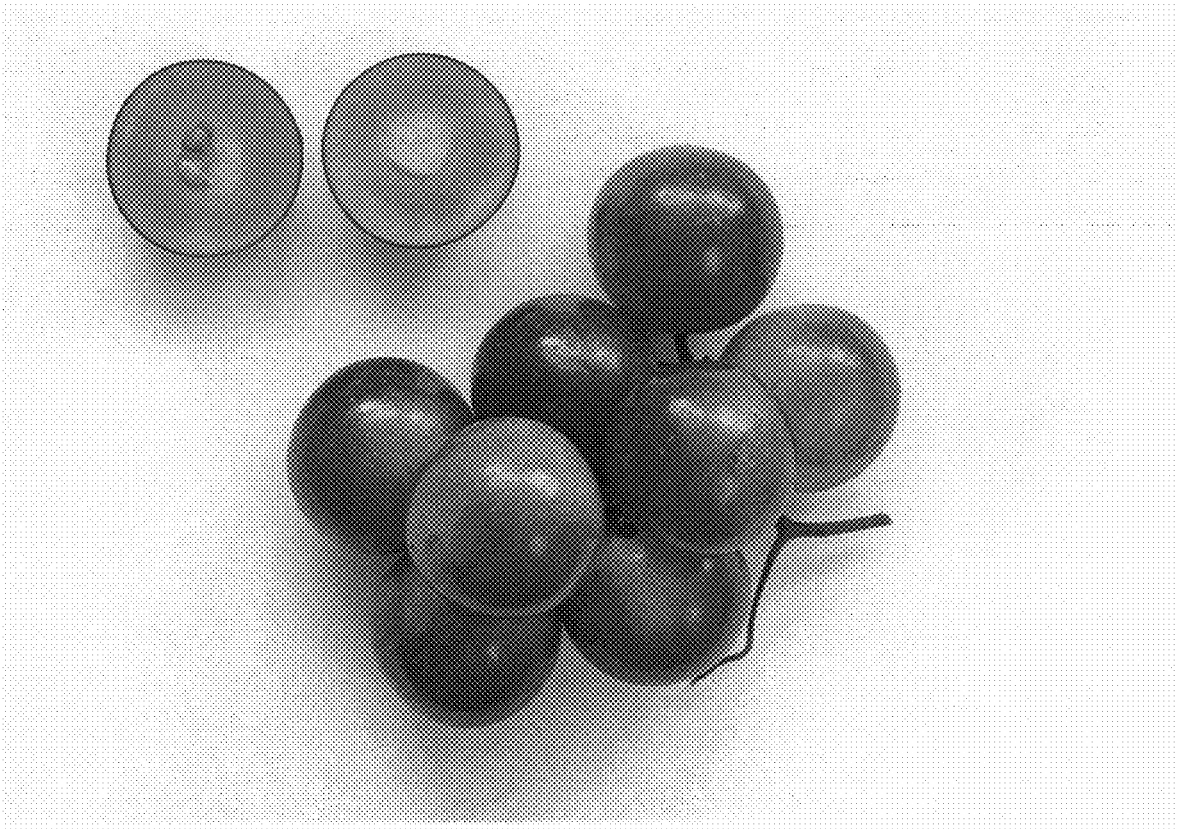
FIG. 1 is view of a ripe 'Ga. 8-1-338' cluster and a single berry which has been cut in half to display skin thickness and interior flesh.

The muscadine grape, *Vitis rotundifolia* Michx., is a popular fresh fruit grown in the Southeastern United States. In the Georgia climate, many cultivars ripen in early autumn when few other fruits are in season. The berries are large, as compared to other grape species, and are typically borne in clusters of 5-7 berries. Like many fruit crops, muscadine grapes are a heterozygous species and superior genotypes are clonally propagated. Nurseries typically propagate this species either by rooting softwood cuttings under mist, or by layering vines in the field.

The muscadine season in South Georgia begins in the last week of July and first week of August. At this time, growers begin picking the earliest ripening berries on the earliest cultivars. Unlike *vinifera* grapes, fresh-market muscadines are typically harvested as single berries by hand. Muscadines can vary in color from greenish-yellow (bronze) to pink, red, and purple, but stores often segregate them out as either bronze or purple/black, the two most common colors. As consumers are often partial to one or the other color, a grower typically would like to have both colors available.

Numerous muscadine cultivars are of commercial importance. One muscadine production guide for Georgia lists 34 fresh market cultivars (nine are categorized as most recommended) and six processed grape cultivars. Even with this large number of cultivars, many are lacking desirable characteristics and growers are very interested in new cultivars with a higher combination of desirable traits. Currently, many commercial vineyards contain primarily female muscadine grape plants with a lesser number of self-fertile cultivars as the pollinator. Female cultivars have a yield that is often only about one-half that of self-fertile cultivars due to lack of pollination (flowers of female cultivars often don't open completely, blocking pollination). Despite the reduced productivity of most female cultivars, growers have continued to grow them because berry size and quality has typically been much larger in female cultivars than in self-fertile cultivars. Generally, growers want a berry size of at least 1 inch (2.5 cm) in diameter in a fresh-market cultivar. Provided minimum size and quality standards are met, more consistently productive self-fertile cultivars would be highly desirable.

DETAILED DESCRIPTION

In the following description, color references are made to The Royal Horticultural Society Colour Chart, copyright 1966, except where general terms of ordinary dictionary significance are used. The description is of a four year old 'Ga. 8-1-338' plant.

An initial cross ('Supreme' x 'Tara') was made by the inventor in Tifton, Ga. as a part of a muscadine grape breeding program. 'Supreme' is the subject of U.S. Plant Pat. No. 7,267 and 'Tara' is unpatented. 'Supreme' is the primary fresh-market purple/black cultivar today. Positive attributes of 'Supreme' are very large berry size, firm flesh, and good flavor. Negative attributes of 'Supreme' are low vine vigor, female flowers and poor cold hardiness. 'Tara' is a plant with hermaphroditic flowers, bronze berries, medium berry size, and early harvest.

Approximately 800 seedlings from this initial cross were germinated in the greenhouse and planted in Tifton, Ga. in the spring of 2009. The original seedling vine of 'Ga. 8-1-338' was selected from these seedlings for hermaphroditic flowers, large berry size, good productivity, a crisp skin and firm flesh and a red berry color noticeably different from either parent.

Cuttings were rooted from the selected seedling of this new variety in Tifton, Ga. Asexually propagated plants of the new variety were planted in trial plantings at two locations in Tifton, Ga. and at one location in Wray, Ga. in 2012. 'Ga. 8-1-338' differs from 'Supreme' in that the vines are hermaphroditic.

Figure 2:
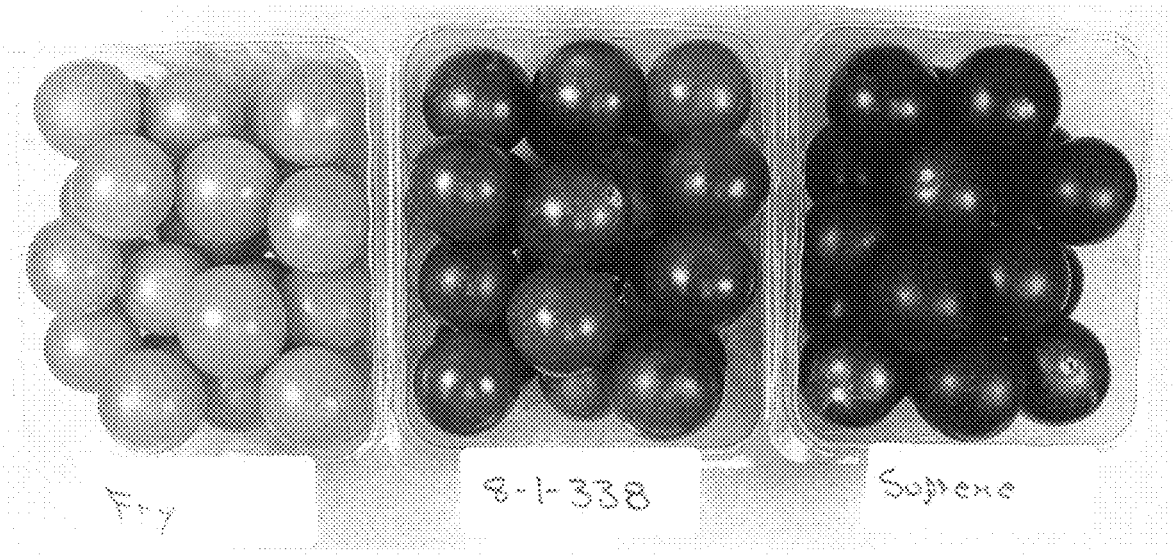
FIG. 2 is a view of ripe 'Ga. 8-1-338' berries (center) in a pint clamshell package in comparison to 'Fry' (unpatented) and 'Supreme' (U.S. Plant Pat. No. 7,267) muscadines which typify muscadine bronze and black colors respectively.

'Ga. 8-1-338' is mid-season muscadine with red colored berries (FIGS. 1, 2) and hermaphroditic flowers. The color of 'Ga. 8-1-338' berries represents a new color class for muscadine grapes. Traditionally muscadines have been classified as bronze, lacking in anthocyanin pigmentation, and fully pigmented black cultivars. In addition, a pink berry color exists which is a bronze berry with a very light purple blush as in the cultivar 'Scarlett' (U.S. Plant Pat. No. 11,260). 'Ga. 8-1-338' is notable in that it had similar L* (lightness) and C* (chroma) value to the bronze colored 'Fry' and in appearance is a more vivid shade of red (higher C*) than the pink-colored 'Scarlett' (Table 1).

Yields of 'Ga. 8-1-338' were very good and are similar to or better than other hermaphroditic cultivars and the high-yielding female 'Supreme' (Tables 2, 3). Usable yield of 'Ga. 8-1-338' was also very good (Tables 2, 3). Percent usable yield was not as good as 'Ga. 6-2-26' (U.S. Plant Pat. No. 30,014) in Tifton, Ga. but was similar to all other cultivars (Table 2). In Wray, Ga. percent usable yield was lower than all other cultivars except 'Fry' (Table 3). Usable yield was lowered by relatively high incidences of berry split and berry rot (Tables 4, 5). Berry weight (15.2-14.5 g) and diameter (30.2-27.5 mm) is excellent and is larger than other hermaphroditic cultivars except the recently released 'Ga. 6-2-26' (Tables 4, 5). Soluble solids of the berry juice was higher than all cultivars except 'Ga. 5-1-45' (U.S. Plant Pat. No. 24,142) in Tifton, Ga. (Table 4) and similar to other cultivars in Wray, Ga. (Table 5).

Figure 3:
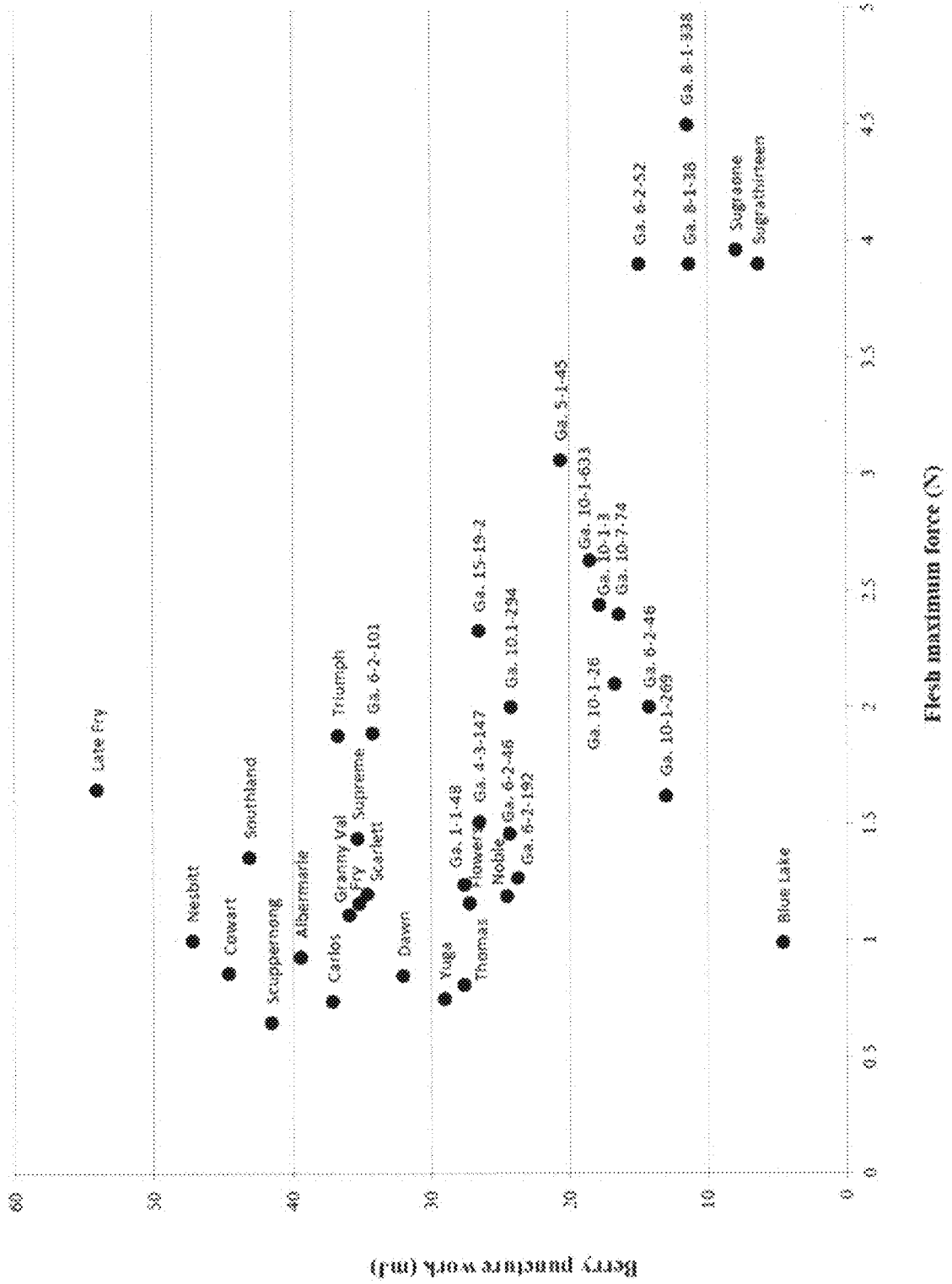
FIG. 3 is a graph displaying berry puncture work for muscadine and euvitis germplasm.
Figure 4:
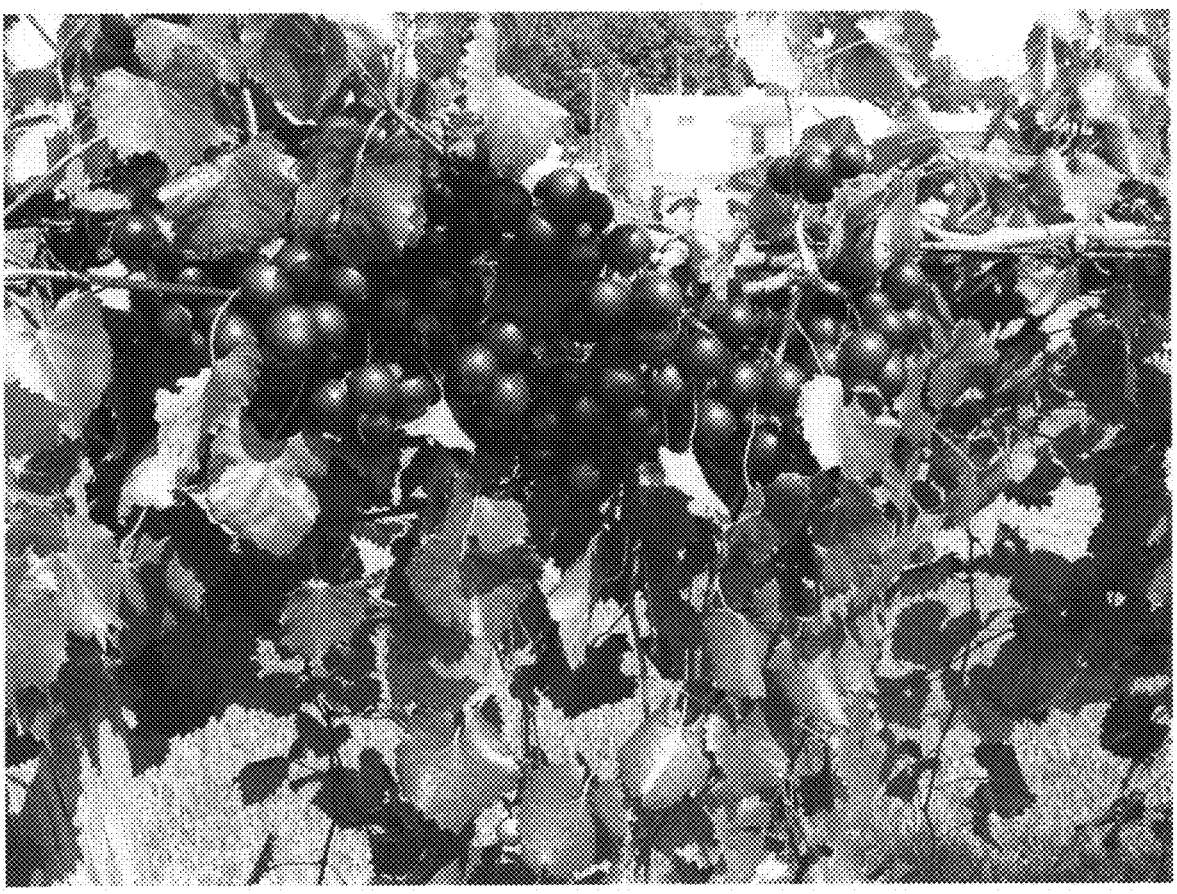
FIG. 4 is a view of a four year old 'Ga. 8-1-338' plant showing its foliage and fruit.

With reference to FIG. 3, berry puncture work is a measure of skin crispness in that the less work to puncture the berry the more crisp a texture that the skin possesses. Flesh maximum force is a measure of flesh firmness and the greater the force the more firm the flesh. 'Ga. 8-1-338' groups in the lower right of the chart, near the *V. vinifera* table grape cultivars 'Sugraone' (U.S. Plant Pat. No. 3,106) and 'Sugrathirteen' (U.S. Plant Pat. No. 10,434) indicating that the new variety has a crisp skin and firm flesh. 'Blue Lake' is an unpatented *vitus labrusca* cultivar similar to 'Concord' (unpatented). The data points in FIG. 3 represent an average of 20 berries measured for each fruit.

In addition to the red berry color, a noticeable attribute of this cultivar is the texture and flavor. 'Ga. 8-1-338' berries have a very crisp skin and firm flesh (FIG. 3). Unlike traditional muscadines, the skin of 'Ga. 8-1-338' is easily masticated as shown by the low level of work for berry puncture shown on the y-axis of FIG. 3. The flesh of 'Ga. 8-1-338' is firmer than even 'Ga. 5-1-45 as shown on the x-axis of FIG. 3. This combination leads to a texture fairly similar to *V. vinifera* table grapes. FIG. 3 has omitted the single quotes around the varietal names for convenience.

The patent status of each of the varieties mentioned in FIG. 3, not described elsewhere in this application is as follows:

'Late Fry' (U.S. Plant Pat. No. 9,224); 'Nesbitt' (Unpatented); 'Southland' (Unpatented); 'Scuppernong' (Unpatented); 'Albermarle' (Unpatented); 'Carlos' (Unpatented); 'Granny Val' (U.S. Plant Pat. No. 5,823); 'Triumph' (Unpatented); 'Ga. 6-2-101' (Unpatented, unreleased selection); 'Dawn' (Unpatented); 'Yuga' (Unpatented); 'Thomas' (Unpatented); 'Flower's (Unpatented); 'Ga. 4-3-147' (Unpatented, unreleased selection); 'Ga. 15-19-2' (Unpatented, unreleased selection); 'Ga. 6-2-46' (Unpatented, unreleased selection); 'Ga. 10-1-294' (Unpatented, unreleased selection); 'Ga. 6-2-192' (Unpatented, unreleased selection); 'Ga. 10-1-633' (Unpatented, unreleased; election); 'Ga. 10-1-26' (Unpatented, unreleased selection); 'Ga. 10-1-3' (Unpatented, unreleased selection); 'Ga. 6-2-46' (Unpatented, unreleased selection); 'Ga. 10-1-269' (Unpatented, unreleased selection); 'Ga. 6-2-52' (Unpatented, unreleased selection); and 'Ga. 8-1-38' (Unpatented, unreleased selection).

Plant Characteristics

Vines: The vines of 'Ga. 8-1-338' grow vigorously and mature canes in Tifton, Ga. are 1.0 to 1.5 m in length per growing season and are greyed-orange in color (RHS 165A). Shoot tips are greyed-orange in color (RHS 174B). Trunk bark color is greyed-orange (RHS 177D) and rough in texture. Internode lengths are 5-6 cm in length. Tendrils are 8-10 cm long and unbranched, and discontinuous along the nodes. Tendril color is orange-red (RHS 35a).

Foliage: Leaves average 60-70 mm in length and 80-90 mm in width. The leaves are cordate to nearly peltate with broadly toothed margins and glabrous on both upper and lower surfaces. Mature upper leaf surface is yellow-green (RHS 146A) and somewhat dull, while lower surfaces are yellow-green (RHS 144A). Petiole length is 4-5 cm and the petiole sinus is sagitate.

Flowers: The flowers are hermaphroditic and approximately 4 mm wide by 3 mm tall. Inflorescences are approximately 3 cm wide and 5 cm tall. The functional yellow-colored anthers (RHS 11C) are supported on long (2.5 mm) filaments at the base of the ovary. The flowers are short lived, lasting approximately 2 to 3 days. 'Ga 8-1-338' typically blooms from May 12th to May 31st at Tifton, GA.

Fruit: The vines produce very large (approx. 15 g) berries with red-purple color (RHS 59A) at the base graduating towards red at the stem end (RHS 46A). The berries ripen over a two-week period beginning the third week of August in Tifton, Ga. The berries are round and average 30 mm in diameter containing an average of 3 seeds per berry. The seeds are yellow-green in color (RHS 152B) when fresh and grey brown in color (RHS 152D) when dried.

Comparisons with Other Muscadine Grape Cultivars

The Tables 1-5 below compare 'Ga. 8-1-338' with some other known muscadine grape cultivars. 'Cowart', 'Fry', 'Noble', 'Regale', 'Tarheel', and 'Tara' are unpatented. 'Ga. 5-1-45' is the subject of U.S. Plant Pat. No. 24,142. 'Ga. 1-1-48' is the subject of U.S. Plant Pat. No. 27,033. 'Ga. 6-2-26' is the subject of U.S. Plant Pat. No. 30,014. 'Supreme' is the subject of U.S. Plant Pat. No. 7,267. 'Scarlett' is the subject of U.S. Plant Pat. No. 11,260.

TABLE 1

CIELAB color parameters of berry skins of Muscadinia clones.

| Clone | Berry color[z] | L*[y] | C*[x] | h°[w] |
|---|---|---|---|---|
| 'Ga 8-1-338' | Red | 47.7 a | 22.8 a | 64.0 ab |
| 'Cowart' | Black | 22.2 c | 7.7 c | 13.7 b |
| 'Fry' | Bronze | 45.6 a | 20.2 a | 91.8 a |
| 'Lake Charles' | Black | 20.4 c | 2.4 e | 13.0 b |
| 'Ga. 5-1-45' | Black | 21.0 c | 3.4 de | 16.9 b |
| 'Noble' | Black | 23.2 c | 6.7 cd | 15.7 ab |
| 'Regale' | Black | 21.3 c | 3.1 de | 30.5 ab |
| 'Scarlett' | Pink | 34.0 b | 16.3 b | 33.3 ab |
| 'Supreme' | Black | 22.2 c | 4.1 cde | 44.4 ab |
| 'Tarheel' | Black | 21.9 c | 3.3 de | 28.8 ab |

[z]Berry color based on visual estimation.
[y]The value of L* describes the degree of darkness or lightness with L = 0 being black and L = 100 white.
[x]Richness of color is represented by C*, with larger numbers indicative of a richer color.
[w]h° represents the dominant color wavelength where 0° = red-purple, 90° = yellow, 180° = bluish-green, 270° = blue.

TABLE 2

Yield (kg/3-m vine) of 'Ga. 8-1-338' and standard muscadine cultivars at Tifton, GA in the third through fifth years of growth (2014-2016).

| Cultivar | No. vines | Total Yield (kg)[z] | Usable yield (kg)[yz] | Percent usable yield[z] |
|---|---|---|---|---|
| Year 3 | | | | |
| 'Ga. 8-1-338' | 4 | 16.4 | 13.0 ab | 79.5 ab |
| 'Fry' | 4 | 11.7 | 7.0 c | 55.9 d |
| 'Ga. 1-1-48' | 4 | 14.6 | 10.3 ab | 74.0 bc |
| 'Ga. 5-1-45' | 4 | 12.9 | 8.4 c | 67.2 cd |
| 'Ga. 6-2-26' | 8 | 17.3 | 15.3 a | 88.7 a |
| 'Supreme' | 4 | 12.8 | 10.3 be | 81.0 ab |
| 'Significance' | | NS | 0.006 | <0.001 |
| Year 4 | | | | |
| 'Ga. 8-1-338' | 4 | 28.1 a | 19.9 a | 71.7 b |
| 'Try' | 4 | 8.7 c | 6.7 b | 77.7 cd |
| 'Ga. 1-1-48' | 4 | 21.2 b | 19.5 a | 92.1 ab |
| 'Ga. 5-1-45' | 4 | 13.5 c | 9.6 b | 71.3 d |
| 'Ga. 6-2-26' | 8 | 20.6 b | 19.2 a | 93.6 a |
| 'Supreme' | 4 | 25.1 ab | 23.0 a | 85.8 bc |
| 'Significance' | | <0.001 | <0.001 | <0.001 |
| Year 5 | | | | |
| 'Ga. 8-1-338' | 4 | 33.0 a | 28.1 a | 85.3 ab |
| 'Fry' | 4 | 13.8 c | 11.6 c | 82.8 bc |
| 'Ga. 1-1-48' | 4 | 22.9 b | 17.7 bc | 76.7 c |
| 'Ga. 5-1-45' | 4 | 20.2 bc | 17.0 bc | 83.6 bc |
| 'Ga. 6-2-26' | 8 | 31.0 a | 28.4 a | 91.7 a |
| 'Supreme' | 4 | 24.0 b | 21.4 b | 88.7 ab |
| 'Significance' | | <0.001 | <0.001 | <0.001 |
| All Years Avg | | | | |
| 'Ga. 8-1-338' | 4 | 25.2 a | 19.6 ab | 78.0 bcd |
| 'Fry' | 4 | 11.4 c | 8.5 d | 72.1 cd |
| 'Ga. 1-1-48' | 4 | 19.3 ab | 15.7 bc | 81.3 bc |
| 'Ga. 5-1-45' | 4 | 15.5 bc | 11.7 cd | 74.1 cd |
| 'Ga. 6-2-26' | 8 | 22.9 a | 21.0 a | 91.3 a |
| 'Supreme' | 4 | 20.7 ab | 17.7 ab | 85.1 ab |
| 'Significance' | | <0.001 | <0.001 | <0.001 |

[z]Mean separation within columns by Duncan's multiple range test, $P < 0.05$.
[y]Usable yield is total yield minus weight of rotted berries and berries with pedicel scar splitting.

TABLE 3

Yield (kg/6.1-m vine), at Wray, GA in the third through fifth years of growth (2014-2016).

| Cultivar | No. vines | Total Yield (kg)[z] | Usable yield (kg)[yz] | Percent usable yield[z] |
|---|---|---|---|---|
| Year 3 | | | | |
| 'Ga. 8-1-338' | 4 | 19.8 abc | 13.3 bc | 69.7 b |
| 'Fry' | 4 | 7.5 c | 5.2 c | 68.9 b |
| 'Ga. 1-1-48' | 4 | 26.9 ab | 22.3 ab | 83.6 a |
| 'Ga. 6-2-26' | 2 | 36.8 a | 33.8 a | 92.2 a |
| 'Supreme' | 4 | 17.7 be | 14.9 bc | 84.9 a |
| 'Significance' | | 0.027 | 0.007 | 0.005 |
| Year 4 | | | | |
| 'Ga. 8-1-338' | 4 | 50.4 b | 29.9 a | 57.1 bc |
| 'Fry' | 4 | 71.9 a | 36.6 a | 51.3 c |
| 'Ga. 1-1-48' | 4 | 20.6 c | 14.3 b | 69.9 b |
| 'Ga. 6-2-26' | 2 | 11.8 c | 10.3 b | 90.5 a |
| 'Supreme' | 4 | 22.1 c | 19.9 b | 89.5 a |
| 'Significance' | | <0.001 | <0.001 | <0.001 |
| Year 5 | | | | |
| 'Ga. 8-1-338' | 4 | 28.7 | 18.9 ab | 62.5 c |
| 'Fry' | 4 | 12.3 | 4.6 b | 33.3 d |

TABLE 3-continued

Yield (kg/6.1-m vine), at Wray, GA in the third through fifth years of growth (2014-2016).

| Cultivar | No. vines | Total Yield (kg)[z] | Usable yield (kg)[yz] | Percent usable yield[z] |
|---|---|---|---|---|
| 'Ga. 1-1-48' | 4 | 27.5 | 23.0 a | 83.8 ab |
| 'Ga. 6-2-26' | 2 | 40.9 | 37.8 a | 92.3 a |
| 'Supreme' | 4 | 30.2 | 22.5 a | 75.1 b |
| 'Significance' | | NS | 0.033 | <0.001 |
| All years avg. | | | | |
| 'Ga. 8-1-338' | 4 | 33.3 | 20.5 | 63.2 c |
| 'Fry' | 4 | 32.2 | 16.4 | 52.8 d |
| 'Ga. 1-1-48' | 4 | 25.0 | 19.9 | 79.1 b |
| 'Ga. 6-2-26' | 2 | 29.8 | 27.3 | 91.7 a |
| 'Supreme' | 4 | 23.3 | 19.1 | 83.1 ab |
| 'Significance' | | NS | <0.001 | NS |

[z]Mean separation within columns by Duncan's multiple range test.

[y]Usable yield is total yield minus weight of rotted berries and berries with pedicel scar splitting.

TABLE 4

Flower and fruit attributes of 'Ga. 8-1-338' and standard muscadine cultivars at Tifton, GA in the third through fifth years of growth (2014-2016).

| Cultivar | Flower type[z] | Berry color | Avg. day of first harvest | Berry rot (%)[y] | Berry stem scar my split (%)[y] |
|---|---|---|---|---|---|
| 'Ga. 8-1-338' | H | Red | Aug. 21 ab | 8.4 bc | 14.9 b |
| 'Fry' | F | Bronze | Aug. 19 b | 12.6 ab | 17.7 ab |
| 'Ga. 1-1-48' | H | Bronze | Aug. 2 c | 16.6 a | 2.6 c |
| 'Ga. 5-1-45' | H | Black | Aug. 4 c | 4.0 c | 22.9 a |
| 'Ga. 6-2-26' | H | Black | Aug. 19 b | 4.7 c | 4.2 c |
| 'Supreme' | F | Black | Aug. 24 a | 3.4 c | 11.9 b |
| 'Significance' | | | <0.001 | <0.001 | <0.001 |

| Cultivar | Berry stem scar tear (%)[y] | Dry scar (%)[y] | Berry wt. (g)[y] | Berry diam. (mm)[y] | Percent soluble solids of all harvests[y] |
|---|---|---|---|---|---|
| 'Ga. 8-1-338' | 34.5 a | 48.7 d | 15.2 a | 30.2 a | 16.1 a |
| 'Fry' | 32.9 ab | 49.4 d | 12.2 b | 27.9 b | 14.5 b |
| 'Ga. 1-1-48' | 6.5 d | 90.9 a | 10.1 c | 26.0 c | 14.9 b |
| 'Ga. 5-1-45' | 25.0 c | 52.2 cd | 9.2 c | 25.4 c | 15.5 ab |
| 'Ga. 6-2-26' | 15.0 a | 84.9 a | 15.0 a | 30.2 a | 14.9 b |
| 'Supreme' | 15.0 a | 59.3 c | 15.0 a | 30.0 a | 14.5 b |
| 'Significance' | <0.001 | <0.001 | <0.001 | <0.001 | 0.017 |

[z](H) hermaphroditic, (F) female

[y]Mean separation within columns by Duncan's multiple range test.

TABLE 5

Flower and fruit attributes of 'Ga. 8-1-338' and standard muscadine cultivars at Wray, GA in the third through fifth years of growth (2014-2016).

| Cultivar | Berry rot (%)[y] | Berry stem scar split (%)[y] | Berry stem scar tear (%)[y] | Dry scar (%)[y] |
|---|---|---|---|---|
| 'Ga. 8-1-338' | 29.6 b | 10.6 | 31.7 ab | 57.7 bc |
| 'Fry' | 41.1 a | 9.6 | 35.8 a | 51.7 c |
| 'Ga. 1-1-48' | 17.7 c | 4.7 | 10.4 c | 85.0 a |
| 'Ga. 6-2-26' | 4.5 d | 4.0 | 11.4 c | 84.6 a |
| 'Supreme' | 7.1 d | 10.6 | 23.8 b | 65.6 b |
| 'Significance' | <0.001 | NS | <0.001 | <0.001 |

| Cultivar | Berry wt. (g)[y] | Berry diam. (mm)[y] | Percent soluble solids of all harvests[y] |
|---|---|---|---|
| 'Ga. 8-1-338' | 14.5 a | 27.5 ab | 15.9 |
| 'Fry' | 10.4 b | 25.3 b | 14.2 |
| 'Ga. 1-1-48' | 10.2 b | 26.3 b | 14.8 |
| 'Ga. 6-2-26' | 15.8 a | 30.6 a | 15.3 |
| 'Supreme' | 15.0 a | 29.3 a | 14.0 |
| 'Significance' | <0.001 | <0.001 | NS |

[z](H) hermaphroditic, (F) female

[y]Mean separation within columns by Duncan's multiple range test.

What is claimed is:

1. A new and distinct muscadine grape plant, substantially as herein illustrated and described, characterized by dark red-colored berries; self-fertile flowers; berries that are very large in size, berries with a firm flesh and crisp skin, and berries with a high soluble solids content.

* * * * *